United States Patent [19]

Sheppard et al.

[11] Patent Number: 6,060,067

[45] Date of Patent: May 9, 2000

[54] PROCESS FOR THE PREPARATION OF TETANUS TOXOID VACCINE

[75] Inventors: Anthony James Sheppard; Peter Anthony Knight, both of Beckenham, United Kingdom

[73] Assignee: Medeva Pharma Limited, Surrey, United Kingdom

[21] Appl. No.: 08/374,649

[22] PCT Filed: May 20, 1993

[86] PCT No.: PCT/GB93/01037

§ 371 Date: Mar. 1, 1995

§ 102(e) Date: Mar. 1, 1995

[87] PCT Pub. No.: WO94/03206

PCT Pub. Date: Feb. 17, 1994

[30] Foreign Application Priority Data

Jul. 31, 1992 [GB] United Kingdom .................... 9216351

[51] Int. Cl.⁷ .......................... A61K 39/00; A61K 39/02; A61K 39/10; A61K 39/108
[52] U.S. Cl. ..................................... 424/239.1; 424/184.1; 424/234.1; 424/236.1; 424/240.1; 424/241.1; 424/253.1; 424/254.1; 424/257.1; 424/261.1; 435/243; 435/252.1; 436/543
[58] Field of Search ............................. 424/239.1, 236.1, 424/184.1, 234.1, 240.1, 241.1, 253.1, 254.1, 257.1, 261.1; 435/243, 252.1; 436/543

[56] References Cited

U.S. PATENT DOCUMENTS 4,996,299  2/1991  Ginnaga et al. .......................... 530/409

FOREIGN PATENT DOCUMENTS 969772   9/1964   United Kingdom .
969772   10/1964  United Kingdom .
9112020  8/1991   WIPO ............................ A61K 39/10
WO 91/12020 8/1991 WIPO .

OTHER PUBLICATIONS

Relyveld et al. Methods in Enzymology 93:24–60, 1983.

Pillemer et al. J. Immunol. 54:213–224, 1946.

Physician's Desk Reference. Medical Economics Data, Oradell NJ. 1991 Edition, pp. 1206–1207.

Rene Germanier, Excerpt from Bacterial Vaccines, 1984, pp. 48–49, 60–61.

Chemical Abstracts, vol. 72, No. 3, Jan. 19, 1970, D.J. Dawson et al 'Tetanus Toxin and Toxoid, IV. Interaction of Foraldehyde With Tetanus Toxin.' p. 172.

Biologicals (1993) 21, Anomalous Symptoms In Mice Injected With Reverte Tetanus Toxoid Knight et al, pp. 183–184.

*Primary Examiner*—James C. Housel
*Assistant Examiner*—V. Ryan
*Attorney, Agent, or Firm*—Nixon & Vanderhye P.C.

[57] ABSTRACT

A process for the preparation of tetanus toxoid, which process comprises incubating purified tetanus toxin with 0.2 to 1% (v/v) formaldehyde in the presence of 0.005 to 0.25M lysine for from 24 to 32 days at a pH of from 6.0 to 8.0 and a temperature of from 30 to 45° C.

10 Claims, No Drawings

PROCESS FOR THE PREPARATION OF TETANUS TOXOID VACCINE

This invention relates to a process for the preparation of tetanus toxin for use in tetanus vaccines.

The existing tetanus vaccine is produced from a 7-day bottle culture of *Clostridium tetani* which is inactivated ("toxoided") by the addition of formaldehyde. The formaldehyde is added as formalin. Toxoid is purified for use in a vaccine by salt fractionation to a specific activity of approximately 1200 flocculation units (Limes flocculationis, Lf)/mg protein nitrogen (PN), which is equivalent to 30% to 40% purity.

Attempts have been made to increase the specific activity of the vaccine by purifying the toxoid using immunoadsorbents (Hughes et al, J. Appl. Bact. 37, 603–621, 1974). This however only resulted in a limited increase, to 1600 Lf/mg PN. GB-A-969772 discloses a method for producing a toxoid from a purified bacterial toxin, especially purified diphtheria toxin, by treating the toxin in an aqueous medium with formaldehyde in the presence of an aliphatic diamine of molecular weight below 200 which contains a primary or secondary amino group. Preferred diamines are lysine and ethylenediamine.

We have now devised a new process for the preparation of tetanus toxoid. Instead of toxoiding the toxin and then purifying the toxoid, we purified the toxin and then toxoided the purified toxin. Surprisingly, however, many of these preparations were found to be unstable, showing varying degrees of reversion to toxicity when stored at 37° C. in the absence of formalin.

We then looked at adding amino acids to the toxoiding reaction at different concentrations, also varying the formalin concentration, pH and incubation times. Reversion to toxicity was difficult to avoid, except at the price of low total combining power (TCP)/Lf ratios that resulted in preparations of poor immunogenicity. Only under specific conditions could stable and highly immunogenic preparations be obtained.

Accordingly, the present invention provides a process for the preparation of tetanus toxoid, which process comprises incubating purified tetanus toxin with 0.2 to 1% (v/v) formaldehyde in the presence of 0.005 to 0.25M lysine for from 24 to 32 days at a pH of from 6.0 to 8.0 and a temperature of from 30 to 45° C.

The tetanus toxin is typically obtained from a culture of *Clostridium tetani*. Any appropriate strain of *Cl. tetani* can be employed. The toxin may be purified from a fermentation broth by first centrifuging the broth and then clarifying the culture supernatant, for example by a two stage filtration. The clarified supernatant may be concentrated. The supernatant may then be subjected to diafiltration to remove small charged molecular species and then to ion-exchange chromatography.

The purified toxin preferably has an Lf content of 250 Lf/ml or more, for example from 250 to 500 Lf/ml. If the Lf content is less than 250 Lf/ml, the toxin may be reprocessed by an additional concentration step to increase the toxin yield.

The specific activity of the toxin may be determined by estimating the protein nitrogen (PN) content of the purified material and by calculating the ratio of Lf to PN. Typically, the purified toxin has a ratio of Lf to PN of 2000 Lf/mg PN or more, for example from 2000 to 3000 Lf/mg PN or from 2000 to 2800 Lf/mg PN. If the specific activity of the toxin is less than 2000 Lf/mg PN, the purified material may be reprocessed through an ion-exchange column. A specific activity of 2000 Lf/mg PN is equivalent to a purity of about 70%. 100% pure toxin is reported to have a specific activity of 3000 to 3200 Lf/mg PN.

The purity of the toxin may alternatively or additionally be assessed by high pressure liquid chromatography (HPLC) analysis and/or by sodium dodecyl sulphate-polyacrylamide gel electrophoresis (SDS-PAGE). Purity is preferably determined by HPLC whereby eluted peaks are integrated and the area of toxin-related peaks is expressed as a percentage of the total integrated peaks area. Analysis by SDS-PAGE under reducing conditions separates the toxin molecule into its constituent heavy (100 kD) and light (50 kD) chains. The two bands can be identified after staining and their combined intensities, as determined by densitometry, are expressed as a percentage of the total bands.

If the HPLC analysis and/or SDS-PAGE analysis shows that the toxin is less than 70% pure, the material can be reprocessed through an ion-exchange column to increase the purity. Preferably therefore the toxin is 70% or more pure, for example from 70% to 100% pure, as determined by HPLC and/or SDS-PAGE. The toxin may be 80% or more pure or 90% or more pure.

The purified tetanus toxin is toxoided by 0.2 to 1% (v/v) formaldehyde in the presence of 0.005 to 0.25M lysine. A buffer such as sodium borosuccinic acid buffer is typically added to adjust the pH of the solution of purified toxin to from 6.0 to 8.0, preferably from 6.5 to 7.5. The concentration of the purified toxin in solution is typically adjusted to from 150 to 300 Lf/ml, preferably about 200 Lf/ml.

Typically the purified toxin is first preincubated with the formaldehyde in the absence of lysine. The purified toxin may therefore be preincubated with the formaldehyde for from 10 minutes to 2 hours at from 30 to 45° C. Preincubation preferably occurs for from 20 to 40 minutes, for example about 30 minutes. The preincubation temperature is preferably 35 to 40° C., for example about 37° C.

Lysine is then added. The lysine is typically L-lysine such as L-lysine monohydrochloride. A buffer such as sodium bicarbonate buffer may be added to adjust the pH. Incubation of the purified toxin with the formaldehyde and the lysine preferably occurs for about 28 days. The incubation temperature is preferably 35 to 40° C., for example about 37° C. The formaldehyde concentration is preferably 0.25 to 0.5% (v/v). The lysine concentration is preferably 0.05 to 0.2M. Suitable conditions are:
0.25% (v/v) formaldehyde with 0.05 to 0.1M L-lysine, and 0.5% (v/v) formaldehyde with 0.1 to 0.2M L-lysine.

The resulting toxoid may then be purified. Residual formaldehyde and lysine are removed. The toxoid may therefore be concentrated by ultrafiltration, diafiltered to remove the residual formaldehyde and lysine and sterilised by membrane filtration. Preferably the Lf to PN ratio of the toxoid is 2000 Lf/mg PN or more, for example from 2000 to 3000 Lf/mg PN or from 2000 to 2800 Lf/mg PN. Also preferably, the toxoid has a purity of 70% or more, for example from 70% to 100%, as determined by HPLC and/or SDS-PAGE. The toxoid may therefore be 80% or more pure or 90% or more pure as determined by HPLC and/or SDS-PAGE. If the Lf to PN ratio is less than 2000 LF/mg PN and/or if the toxoid is less than 70% pure as determined by HPLC and/or SDS-PAGE, the toxoid may be reprocessed through an ion-exchange column.

A tetanus toxoid according to the invention may therefore not revert to toxin when stored at 37° C. for 3 months or more, preferably for up to 6 months; has a specific activity of from 2000 to 2800 Lf/mg PN, for example 2400 to 2700 LF/mg PN; and has a potency of 130 to 270 International units (Iu)/3.5 Lf, for example 200 to 250 Iu/3.5 Lf.

The resulting toxoid does not revert to toxicity and is more immunogenic than the existing vaccine. The toxoid may therefore be formulated with a pharmaceutically acceptable carrier or diluent to form a vaccine composition. The toxoid may be mixed with a physiologically acceptable solvent such as physiological saline. The toxoid alternatively may be precipitated on or adsorbed by a suitable mineral carrier in a physiological saline or another suitable solution isotonic with blood. Such formulations are generally stored at from 2 to 8° C. prior to use. Thiomersal may be present in the vaccine formulation. The toxoid may be part of a multi-component vaccine, such as a combined diphtheria-tetanus vaccine or a combined diphtheria-tetanus-pertussis vaccine.

A human may therefore be immunised against tetanus by administration of an effective amount of the present tetanus toxoid. Typically, administration is achieved intramuscularly or subcutaneously. In either case, the initial dose of toxoid administered may be from 3 Lf to 10 Lf. That dose may be repeated up to twice at intervals of 2 months. A booster dose of 3 Lf to 10 Lf may be given 5 or 10 years later.

The following Example illustrates the invention. A Reference Example and Comparative Examples are also provided.

REFERENCE EXAMPLE

Preparation of Purified Tetanus Toxin

Cl. tetani strain CN 3911, which is a sub-culture from the Harvard strain of Cl. tetani (Mueller and Miller, J. Immunol. 50, 377–384, 1945), was cultured in modified Meuller's medium (Latham et al, Appl. Microbiol. 10, 146, 1962). More specifically, 10% (v/v) of 48 hour seed culture was used to inoculate either a static bottle or a controlled fermenter containing modified Mueller's medium. In the case of static culture, aluminium powder was added to the medium prior to inoculation. The fermenter, a 15l fermenter, was stirred at 50 rpm and 0.2 uM filtered air drawn across the surface of the culture at a rate of 500 ml/min. Fermentation in the static bottle or in the fermenter was continued for 4 to 7 days at 33±2° C.

The fermentation broth was separated by batch centrifugation (6×1 liter rotor) at 3000 g for 40 minutes. The supernatant was further clarified by a two stage filtration through a 1.2/0.8 μm combination filter and then a 0.2 μm sterile filter.

The culture supernatant was then concentrated ten-fold using a 30K cut-off ultrafiltration membrane and then extensively diafiltered using the same membrane using 10 volumes of buffer [20 mM Tris, 25 mM NaCl, 0.2 mM ethylenediaminetetraacetic acid (EDTA) pH 7.5]. This resulted in an eighteen-fold increase in purity as determined by HPLC. The mean recovery from this step was found to be 80%.

The filtered material was then loaded onto an anion ion-exchange column (DEAE Sepharose Fast Flow). The column was washed with 20 mM Tris buffer, pH 7.5. Tetanus toxin was eluted with 80 mM NaCl, Tris buffer, pH 7.5. The eluted material was sterile filtered through a 0.2 μm sterile filter. The thus-purified material was subjected to the following tests:

(i) ESTIMATION OF Lf CONTENT

This test monitored the toxin yield of the purified toxin material. Approximately 5 ml of purified toxin material was taken for testing. The sample was not stored prior to testing. Lf determination was carried out by the procedure described in Ramon, G. (1922) Sur une technique de titrage in vitro due serum anti-diphtherique. C.P. SOC. BIOL. (Paris) 86, 711–712. The Lf content of the purified material was 250–500 Lf/ml.

(ii) ESTIMATION OF LF:PROTEIN NITROGEN RATIO

This test determined the purity of the purified material. Not less than 1 ml of the purified material was taken for testing. The sample was stored at 5° C.±3° C. if not tested immediately. Protein nitrogen (PN) content was estimated using the Kjeldahl digestion technique (Kjeldahl J. (1888) C.R. CARLSBERG LABOR. (Copenhagen) 2, 1–12) after precipitation with trichloroacetic acid. The ratio of Lf:PN was 2000–3000 Lf/mg PN.

(iii) DETERMINATION OF HPLC PROFILE BY SIZE EXCLUSION

This test ensured that the HPLC profile of the purified toxin was within acceptable limits. Not less than 1 ml purified material was taken for testing. The sample was stored at +4° C. prior to testing. A sample of the purified toxin material is applied to a HPLC gel filtration column (TSK G 3000 SW×1). The separation of sample components is monitored at 280 nm and peak areas integrated. HPLC results:

peak 1 (retention time 10.6–10.7 minutes)-toxin monomer;
peak 2 (retention time 12.4–12.5 minutes)-toxin fragment C; and
peak 3 (retention time>14 minutes)-contaminants.

The combined integrated areas of peaks 1 and 2 was 70 to 100% of the total integrated areas of peaks 1 to 3.

(iv) DETERMINATION OF SDS-PAGE PROFILE

This test ensured that the SDS-PAGE profile of the purified toxin was within acceptable limits. Not less than 0.5 ml of the purified toxin material was taken for testing. The sample was stored at 4° C. prior to testing. The sample was examined, after reduction using mercaptoethanol, by SDS-PAGE by the method described by Laemili (Nature, 227, 680–685, 1970). The gel was scanned by a densitometer and peak areas integrated. Toxin heavy (100 kD) and light (50 kD) bands represented 70 to 100% of total bands stained with Coomassie blue, calculated from the integrated areas detected by densitometry.

EXAMPLE

Toxoiding of Purified Tetanus Toxin

The purified tetanus toxin from the Reference Example was diluted with sufficient sodium borosuccinic acid (SBSA) buffer pH 7.5 to give a final toxin concentration of 200 Lf/ml. Aliquots were toxoided as follows:

1. 0.25% (v/v) formaldehyde in the form of formalin was added to one aliquot and the mixture was preincubated for 30 minutes at 37° C. L-lysine monohydrochloride was subsequently added to a final concentration of 0.05–0.1M, in the presence of 0.1M sodium bicarbonate. The pH of the reaction mixture was from 6.5 to 7.5 and toxoiding was allowed to proceed for 28 days at 37° C.±2° C.

2. 0.5% (v/v) formaldehyde in the form of formalin was added to another aliquot and the mixture was preincubated for 30 minutes at 37° C. L-lysine monohydrochloride was subsequently added to a final concentration of 0.1 to 0.2M, in the presence of 0.1M sodium bicarbonate. The pH of the reaction mixture was from 6.5 to 7.5 and toxoiding was allowed to proceed for 28 days at 37° C.±2° C.

The Lf content of the incubated material was tested as described in the Reference Example. The incubated material was concentrated by ultrafiltration 30K cut-off utrafiltration memebrane. The concentrate was diafiltered using the same 30K membrane, against SBSA buffer pH 7.5, to remove residual formaldehyde and lysine. Thiomersal (ethylmercurithiosalicylic acid, sodium salt) was added to give a final concentration of 0.1 g/liter ($2.5 \times 10^{-4}$ mol/liter) thiomersal. The resulting solution was sterilised by membrane filtration (0.2 µm membrane). Samples were taken and tested as follows:

(i) ESTIMATION OF PROTEIN NITROGEN CONTENT

This test was conducted as described in the Reference Example. The result was 2000–2800 Lf/mg PN.

(ii) ESTIMATION OF TOTAL COMBINING POWER (TCP)

This test determined the antigen content of the tetanus toxoid. TCP is a well used term in the tetanus field, and is referred to in the WHO manual (11, Appendix T.10). It is defined as the reciprocal of the volume of toxoid which when diluted is found to be equivalent to one International Unit (WHO BLG/UNDP/77.1 Rev.1). The quality of toxoids can be measured by determination of the ratio of TCP (binding units) to Lf units, which should be greater than one.

Not less than 5.0 ml of the toxoid was taken for testing. The sample was stored at 5° C.±3° C. if not tested immediately. A suitable range of volumes 0.01–0.03 µl of test material and a reference tetanus toxoid 87 International units (Iu)/ml forming a corrected geometric progression was dispensed into a series of tubes. A fixed dose of 2 Iu/0.5 ml of reference tetanus antitoxin solution was added to each tube and held at room temperature for 60 minutes.

A volume of tetanus test toxin equivalent to one half of the antitoxin dose was added to each tube and allowed to stand for 30 minutes. The contents of each tube were injected subcutaneously into mice each weighing 18–22 g. The mice were observed for 4 days, for signs of typical tetanus paralysis.

If specific tetanus paralysis occurred within 3 days, the test material contained tetanus toxoid equivalent to more than one half of the antitoxin dose added. If the mouse survived for more than 3 days without specific tetanus paralysis, the test material contained tetanus toxoid equivalent to less than one half of the antitoxin dose added. The achievement of specific tetanus paralysis on the third day indicated that the volume of tetanus toxoid was taken to be exactly equivalent to one half of the antitoxin dose added.

Results were accepted as the average of two tests provided that these did not differ by more than 20% of the mean value. The results were 200–350 u/ml.

(iii) ESTIMATION OF Lf CONTENT

The Lf content was determined as described in the Reference Example. Results were 150–250 Lf/ml.

(iv) DETERMINATION OF HPLC PROFILE

HPLC profile was determined as described in the Reference Example. The result was 70–100% purity.

(v) TEST FOR REVERSION

This test demonstrated freedom from reversion of the toxoid to toxin during storage or use and satisfies the requirements of WHO Technical Report Series No. 725, p. 67. 10 ml of diafiltered toxoid material was taken and stored at 5±3° C. until the Lf content had been estimated as described above. The sample was diluted to 16 Lf/ml. The diluted sample was held at 37° C. The sample was tested for non-toxicity after storage for 6 weeks, 2 months and 3 months. 5 ml of the sample was inoculated by the subcutaneous route into each of 2 healthy guinea pigs. The animals were observed for 14 days for death or signs of specific paralysis. There was no evidence of reversion to toxin.

(vi) CHARACTERISATION OF TOXOID BY ELECTROPHORETIC MOBILITY

This test predicted the potency of the toxoided material. 0.5 ml of diafiltered toxoid material was taken for testing. The sample was stored at 5±3° C. if not tested immediately. Glass plates were covered (0.18 ml/cm$^2$) with 1% (v/v) agarose in 60 mM tris buffer pH 8.6. Samples (5 ul) were electropheresed in the first dimension at 20 volts/cm for 60 min. Electrophoresis in the second dimension, into agarose containing horse anti-tetanus serum (0.06% v/v), was carried out at 6 volts/cm for 16 hours.

The gel was stained with Coomassie Blue and mobility of the toxoid peak from the origin was measured. The results, including the result of a reference toxoid (14 mm), were 5–30 mm.

(vii) TEST FOR POTENCY

This test satisfies the requirements of British Pharmacopoiea (1980), Vol. II, p.880, Ph. Eur., Suppl. to Vol. III (1977), p.175 and WHO Technical Report Series No. 638, p.90, Section A.3.5.6. Potency was determined from the response to immunisation with a vaccine prepared by adsorbing the toxoided material onto an adjuvant (aluminium hydroxide, Alhydrogel).

A sample from a transit container of final bulk adsorbed vaccine was taken for testing. The sample was stored at 5° C.±3° C. if not tested immediately. The sample was tested by the method described in Ph. Eur., Suppl. to Vol. III (1977), p.175. Potency was determined as 130 to 270 Iu/3.5 Lf which is significantly higher than the potency of 70–110 Iu/7 Lf of the current vaccine prepared by toxoiding with formaldehyde and then purifying the toxoid.

(viii) TEST FOR SPECIFIC TOXICITY

This test is based upon the requirements of British Pharmacopoiea (1988), Vol. II, p. 1062; Ph. Eur., 1985, p. 452 and WHO Technical Report Series No. 638, p.90, Section A.3.5.5. The test confirmed the absence of detectable toxicity attributable to the tetanus toxoid. Not less than 12.5 ml of toxoided material was taken for testing. The sample was stored at 5° C.±3° C. if not tested immediately. The method was based on that described in Ph. Eur., 1985, p. 452. 1 ml of a dilution containing at least 500 Lf units tetanus toxoid was injected subcutaneously into each of five normal guinea-pigs, each weighing 250 g–350 g. The animals were observed for 21 days for signs of specific toxicity or paralysis. There was no evidence of toxicity attributable to tetanus toxoid.

COMPARATIVE EXAMPLE 1

Toxoiding in Absence of Lysine

The purified tetanus toxin of the Reference Example was toxoided by addition of formalin alone. 0.25–1.0% fomaldehyde in the form of formalin was incubated with toxin at 200 Lf/ml for 14 days at 37° C.±2° C. No lysine was therefore added.

The resulting toxoids were tested for reversion as described in the Example. The toxoids had reverted to toxicity. The reverted toxin in fact rarely induced classical tetanus but produced a different neurological syndrome.

COMPARATIVE EXAMPLE 2

Toxoiding in the Presence of Lysine Under Different Conditions

The purified tetanus toxin of the Reference Example was toxoided as follows:

(i) Purified tetanus toxin from the Reference Example was diluted with sufficient SBSA buffer pH 7.5 to give a final toxin concentration of 200 Lf/ml. 0.1 to 1.0% formaldehyde, in the form of formalin, was added to an aliquot and the mixture was preincubated for 30 minutes at 37° C. L-lysine monohydrochloride was subsequently added to a final concentration of 0.005 to 0.1M, in the presence of 0.1M sodium bicarbonate. The pH of the reaction mixture was from 6.5 to 7.5 and toxoiding was allowed to proceed for 14 days at 37° C.

(ii) As (i) but pH of the toxoiding reaction was varied from 6.0 to 8.5.

(iii) As (i) but arginine (0.05 to 0.1M) was used in place of lysine.

(iv) As (i) but incubation period was increased from 14 days to 21 days.

(v) As (i) but no preincubation period.

All the resulting toxoids were tested for reversion as described in the Example. The toxoids had reverted to toxicity.

What is claimed is:

1. A process for the preparation of tetanus toxoid, which process consists essentially of incubating purified tetanus toxin having a specific activity of 2000 Lf/mg PN (Limes flocculationis/mg protein nitrogen) or more and an Lf content of 250 Lf/ml or more with 0.2 to 1% (V/V) formaldehyde in the presence of 0.005 to 0.25M lysine for from 24 to 32 days at a pH of from 6.0 to 8.0 and a temperature of from 30 to 45° C. wherein the toxoid does not revert to toxin when stored at 37° C. for 3 months.

2. A process according to claim 1, wherein the tetanus toxin has been purified from a culture of *Clostridium tetani*.

3. A process according to claim 1, wherein the purified toxin has a specific activity from 2000 to 3000 Lf/mg PN and an Lf content from 250 to 500 Lf/ml.

4. A process according to claim 1, wherein the purified toxin is 80% or more pure as determined by high pressure liquid chromatography and/or sodium dodecyl sulphate-polyacrylamide gel electrophoresis.

5. A process according to claim 1, wherein the purified toxin is preincubated with the formaldehyde in the absence of the lysine for from 20 to 40 minutes at from 35 to 40° C.

6. A process according to claim 1, wherein the purified toxin is incubated with the formaldehyde and lysine for about 28 days at 35 to 40° C.

7. A process according to claim 1, wherein 0.25 to 0.5% (v/v) formaldehyde is employed in the incubation step.

8. A process according to claim 1, wherein 0.05 to 0.2M lysine is employed in the incubation step.

9. A process according to claim 1, wherein the toxoided toxin is formulated with a pharmaceutically acceptable carrier or diluent to form a vaccine composition.

10. A process for the preparation of tetanus toxoid which process consisting essentially of:

a) preincubating purified tetanus toxin having a specific activity of 2000 Lf/mg PN (Limes flocculations/mg protein nitrogen) or more and an Lf content of 250 Lf/ml or more with 0.2 to 1% (v/v) formaldehyde in the absence of lysine for from 20 to 40 minutes at from 35 to 40° C.; and b) incubating the preincubated toxin with 0.2 to 1% (v/v) formaldehyde in the presence of 0.005 to 0.25%M lysine for from 24 to 32 days at a pH of from 6.0 to 8.0 and a temperature of from 30 to 45° C.

\* \* \* \* \*